(12) United States Patent
Grandics

(10) Patent No.: US 6,745,903 B2
(45) Date of Patent: Jun. 8, 2004

(54) METHODS FOR THE ON-LINE, ON-DEMAND PREPARATION OF STERILE, WATER-FOR-INJECTION GRADE WATER

(76) Inventor: Peter Grandics, 5922 Farnsworth Ct., Carlsbad, CA (US) 90720

(*) Notice: Subject to any disclaimer, the term of this patent is extended or adjusted under 35 U.S.C. 154(b) by 0 days.

(21) Appl. No.: 10/099,129

(22) Filed: Mar. 14, 2002

(65) Prior Publication Data

US 2003/0173297 A1 Sep. 18, 2003

(51) Int. Cl.⁷ .......................... C02F 1/76; B01D 15/00
(52) U.S. Cl. ...................... 210/501; 210/660; 210/668; 210/669; 210/663; 210/753; 210/650; 210/651; 252/186.34; 252/187.2
(58) Field of Search .................. 210/650, 651, 210/652, 660–700, 749, 753, 764, 198.2, 501, 503; 252/186.34, 186.36, 187.1, 187.2, 397, 402, 406

(56) References Cited

U.S. PATENT DOCUMENTS

| | | | |
|---|---|---|---|
| 3,959,128 A | | 5/1976 | Harris |
| 4,495,067 A | | 1/1985 | Klein et al. |
| 4,594,392 A | * | 6/1986 | Hatch ...................... 525/327.1 |
| 4,610,790 A | | 9/1986 | Reti et al. |
| 5,061,367 A | * | 10/1991 | Hatch et al. ................. 210/137 |
| 5,366,636 A | | 11/1994 | Marchin et al. |
| 5,517,829 A | | 5/1996 | Michael |
| 5,635,063 A | | 6/1997 | Rajan |
| 6,106,723 A | | 8/2000 | Grandics et al. |
| 6,106,773 A | * | 8/2000 | Miekka et al. ................. 422/28 |

OTHER PUBLICATIONS

Lonnemann, et al., "Quality of water and dialysate in haemodialysis", Nephrology Dialysis Transplantation, Jun. 1996, pp. 946–949, vol. 11, No. 6.

Smith, et al., "March's Advanced Organic Chemistry: Reactions, Mechanisms, and Structure", 2001, pp. 1544–1568.

* cited by examiner

Primary Examiner—W. L. Walker
Assistant Examiner—Krishnan S Menon
(74) Attorney, Agent, or Firm—Michael B. Farber, Esq.; Catalyst Law Group

(57) ABSTRACT

A new method is described to produce large volumes of low cost sterile, Water-for-Injection (WFI) grade water on-line, on-demand from potable water in order to meet the needs of dialysis therapies and other biological applications for sterile, injectable grade water. The source water is processed by a combination of membrane and column chromatographic methods including reverse osmosis, chemical sterilization, reduction of iodine sterilant to iodide, deionization, endotoxin-specific adsorption and polishing filtration in order to reduce contaminant levels below those specified by the US Pharmacopoeia.

16 Claims, 2 Drawing Sheets

Endotoxin Levels of Potable (Tap) Water and Reverse Osmosis Water

METHODS FOR THE ON-LINE, ON-DEMAND PREPARATION OF STERILE, WATER-FOR-INJECTION GRADE WATER

BACKGROUND OF THE INVENTION

General Background and State of the Art

This invention is directed to methods for the on-line, on-demand preparation of sterile, water-for-injection grade water and water preparations produced by such methods.

In the first decades of artificial kidney treatment, technical efforts focused on developing effective dialysis membranes, machines and water systems. In the 1970s, some articles discussing the importance of pyrogenic reactions during hemodialysis induced installation of reverse osmosis systems for preparation of more pure dialysis fluid. In the last decade, growing knowledge of the function of endothelial cells and their role in disease has helped to understand the possible alterations in endothelial cell structure and function evoked by uremia and its dialytic therapy.

Factors injuring the vascular endothelium during hemodialysis include complement activation due to membrane contact, bacterial endotoxins, endotoxin containing immunocomplexes, hyperlipidemia, and cell adhesions. The activated monocytes migrate through endothelial intracellular junctions becoming macrophages; the filtered LDL particles transform them into foam cells. Bacterial endotoxin activates monocytes and the other white blood cells, increasing the chance for endothelial cell injury, arteriosclerosis and inflammatory problems such as amyloidosis.

Many studies emphasize the importance of endotoxin-free dialysate and conclude that finding of transmembrane passage of low molecular weight intact species of LPS that are found in clinically used dialysates emphasizes the importance of obtaining LPS-free dialysates in order to improve the biocompatibility of hemodialysis (for a review, see Lonnemann, G. et al., Nephrol. Dial. Transplant. (1996) 11:946–949).

Other types of renal replacement therapies such as CRRT or hemodiafiltration require sterile replacement fluid that must also be apyrogenic. These therapies are supplied with these solutions in a pre-packaged format at a significant cost. This substantially contributes to the inadequate usage of these therapeutic modalities even if they were more desirable from the patient's point of view.

It has been demonstrated that bacterium and endotoxin-free dialysate resulted in reduced activation of monocytes and lower levels of interleukins and tumor necrosis factor in the patient's blood. Therefore, it is expected that regular use of sterile and endotoxin-free dialysate will help decrease the cardiovascular morbidity and mortality rate of patients undergoing hemodialysis. Since more than 50 percent of the patient population undergoing dialysis treatment is less than 65 years old, preserving their ability to work is very important. Procedures helping to slow the progression of cardiovascular diseases in patients undergoing hemodialysis will help decrease the cost of treatment and may improve the success of renal transplantation.

There is a need to develop a new technology for producing ultrapure, sterile water (preferably of water-for-injection quality) for kidney replacement therapy without significantly affecting the cost of dialysis treatment. The source water for dialysis is potable water. Even after treatment by the water companies, potable water, although safe to drink, contains low levels of mineral salts, trace metals, organic compounds, dissolved gases and colloidal matter, together with particles in suspension and microorganisms. Moreover, unlike other raw materials, water supplies vary widely in quality, both geographically and seasonally.

Before water can be used in the manufacture of pharmaceuticals, it must be purged of its impurities to a degree that is defined by the pharmacopoeias and regulatory authorities like the FDA. The most widely used and accepted method to produce water-for-Injection (WFI) is distillation. The use of distillation makes WFI expensive. The quality of WFI is defined in terms of acceptable limits for inorganic and organic impurities determined by specific physical and chemical tests. WFI must be apyrogenic and free from suspended particles. The FDA recommends that the bacterial count should be below 10 CFU/100 ml. WFI must have a conductivity, measured on-line, less than 1.3 $\mu$S/cm at 25° C. However, the acceptable conductivity range of off-line samples, taking into account pH (which must lie between 5.0 and 7.0), temperature and carbon dioxide equilibrium, is likely to be 2.1 to 4.7 $\mu$S/cm. The maximum acceptable total organic carbon (TOC) level is 500 parts per billion.

The modern approach to purifying water for pharmaceutical applications is to use systems incorporating synergistic combinations of purification technologies. These technologies fall into two broad groups: ion-exchange and membrane processes. The major ion-exchange technique is deionization, using both cation-exchange and anion-exchange resins, while the principal membrane processes are reverse osmosis (RO), ultrafiltration (UF) and microfiltration (MF). The hybrid technology called electrodeionization (EDI) utilizes both ion-selective membranes and ion-exchange resins. These methods are then combined with distillation to produce WFI.

There are prior art methods describing the production of WFI without distillation. Reti and Benn (U.S. Pat. No. 4,610,790) disclosed a method using a plurality of filtration and deionization steps producing sterile water corresponding to USP XX specifications. Klein and Beach (U.S. Pat. No. 4,495,067) disclosed a similar system for making pyrogen-free water. Despite these advances in membrane technology for pyrogen removal, distillation remained the method of choice for WFI. Another invention concerning endotoxin removal from biological fluids was disclosed by Harris (U.S. Pat. No. 3,959,128). He employed non-ionogenic hydrophobic synthetic polymers to adsorb endotoxin from biological fluids.

The literature quoted here points out the complexity of the spectrum of pyrogens present in water and dialysate. The discovery of the heat-stable, low molecular weight pyrogen (s) from Pseudomonas questions the efficacy of ultrafiltration as a tool for pyrogen removal. There is no evidence that the method of Harris would be useful in this regard either.

Renal replacement therapies require high volumes of pure water at a low cost. The high cost of producing large volumes of WFI by the standard technique (distillation) precluded its use in artificial kidney therapies even though it is warranted clinically. It would be desirable to develop a system capable of producing on-line WFI quality water at a low cost from potable water in volumes necessary to meet the needs of dialysis units.

Membrane and particle-based water purification methods are not 100% efficient in eliminating microorganisms. Therefore a high throughput sterilization method is essential to ensure sterility of the purified water product. The sterilizing medium must be in a solid phase in order to minimize contamination of the water to be sterilized as any additive must be removed at the end if the quality criteria for WFI are to be met.

Halogens, such as chlorine and iodine, have demonstrated their utility in destroying microorganism contamination in water. Iodine is more useful in this regard because it can be immobilized to solid phase adsorbents that minimize iodine carryover into the water product. These solid phases are primarily strong anion exchangers. An example is taught by Rajan, U.S. Pat. No. 5,635,063. The iodine released from the adsorbent must subsequently be removed.

One such method is using immobilized silver compounds such as in U.S. Pat. No. 5,635,063 or U.S. Pat. No. 5,366,636. This is an expensive method and may potentially release silver into the water stream, which would be highly undesirable. Another method involves the reduction of iodine with e.g., sulfur dioxide as described in U.S. Pat. No. 5,356,611. The continuous, on-line reduction of iodine by the addition of external reagents would require complicated process controls and equipment. The oxidized form of the added substance must then be removed. This would defeat the objective of a low-cost process.

Therefore, a novel method has been developed to solve this problem and set up an integrated water purification system capable of producing sterile WFI-grade water in an on-line, on-demand system.

INVENTION SUMMARY

Pursuant to this invention a new technique is described to produce large volumes of low cost sterile Water-for-Injection grade water directly from potable water in order to meet the needs of artificial kidney therapies and other biological applications. In an illustrative embodiment, the water is treated by a membrane, a chemical sterilizer, an ion exchanger, and an endotoxin-specific adsorption process in order to reduce contaminant levels below those specified by the US Pharmacopoeia.

In general, a method according to the present invention comprises:

(1) filtering the water by membrane filtration;
(2) sterilizing the water by chemical sterilization using solid phase iodine;
(3) reducing iodine released from the solid phase iodine to iodide;
(4) deionizing the water to remove iodide, residual dissolved salts, and endotoxin; and
(5) removing pyrogens by perfusion through an adsorbent that removes pyrogens.

Typically, the method further comprises the step of filtering the water after removal of pyrogens in step (5) by a final filtration step.

Typically, the membrane filtration of step (1) is performed by reverse osmosis, ultrafiltration, or nanofiltration.

Typically, the chemical sterilization using solid phase iodine is performed on an immobilized iodine column. Preferably, the immobilized iodine column is prepared by adsorbing $KI_3$ to an agarose-based strong anion exchanger containing quaternary amine groups.

Typically, the immobilized iodine column is prepared by adsorbing $KI_3$ to an agarose-based strong anion exchanger containing tertiary amine groups.

Typically, the adsorbent that removes pyrogens is a polymeric support derivatized with a multiplicity of ligands that comprise a ($C_{10}$–$C_{24}$) alkylamino group and that specifically bind endotoxin. Preferably, the alkylamino group is a stearylamino group. Preferably, the polymeric support is agarose. Preferably, the agarose is cross-linked. Preferably, the adsorbent removes pyrogens below the level of 0.25 EU/ml. More preferably, the adsorbent removes pyrogens below the level of 0.005 EU/ml.

A particularly preferred method according to the present invention comprises:

(1) filtering the water by membrane filtration;
(2) sterilizing the water by chemical sterilization using solid phase iodine on an immobilized iodine column prepared by adsorbing $KI_3$ to an agarose-based strong anion exchanger containing tertiary amine groups;
(3) reducing iodine released from the solid phase iodine to iodide by using a solid phase adsorbent that has thiol groups on an agarose-based adsorbent;
(4) deionizing the water to remove iodine, residual dissolved salts, and endotoxin;
(5) removing pyrogens by perfusion through an adsorbent that removes pyrogens that is a polymeric cross-linked agarose support derivatized with a multiplicity of ligands that comprise a stearylamino group and that specifically bind endotoxin to remove pyrogens below the level of 0.005 EU/ml; and
(6) filtering the water after removal of pyrogens in step (e) by a final filtration step.

BRIEF DESCRIPTION OF THE DRAWINGS

These and other features, aspects, and advantages of the present invention will become better understood with reference to the following description, appended claims, and accompanying drawings where:

DESCRIPTION OF THE PREFERRED EMBODIMENTS

Pursuant to this invention a water purification system is described to produce sterile, Water-for-Injection (WFI) quality water inexpensively, on-line, on-demand from potable water. At present the production of WFI is a complex process with several purification steps including membrane filtration, ion exchange and distillation. Distillation is the most widely used final water purification step ensuring an apyrogenic product substantially free from dissolved and particulate contaminants.

Distillation is a low throughput, energy and capital-intensive operation. The capital expense of WFI production system having a capacity of about 10,000 L of WFI per day, one that covers the needs of a hemodialysis unit, is about $300,000 to $400,000 depending on the features. This is a very high start-up cost and also requires the construction of a separate building for housing. The cost of WFI produced by distillation may be as high as $1/L. This cost is prohibitively expensive for hemodialysis clinics.

The system of the subject invention utilizes a chemical solid-phase sterilant to sterilize water and uses both membrane filtration and ion exchange as purification steps to remove most of the dissolved and particulate contaminants from the potable water source. The high-cost distillation step is replaced by a column-based method to remove residual pyrogenic substances from the water using an adsorbent that removes pyrogens. Preferably, the adsorbent that removes pyrogens is a polymeric support derivatized with a multiplicity of ligands comprising a ($C_{10}$–$C_{24}$) alkylamino group and that specifically bind endotoxin. Preferably, the alkylamino group is a stearylamino group. Preferably, the polymeric support is agarose. At least a portion of the ligands can be crosslinked, such as by the use of 2,3-dibromopropanol. When the support is in the form of particles, the particles are preferably from about 20 to about 900 microns in diameter; more preferably, the particles are from about 60 to about 100 microns in diameter. Suitable adsorbents are disclosed in U.S. Pat. No. 6,106,723 to Grandics et al., which is incorporated herein in its entirety by this reference. A particularly preferred adsorbent is the adsorbent marketed as ClarEtox™, Clarigen, Inc., Carlsbad, Calif. Further details as to the use of ClarEtox are given in the Examples.

Figure 1:
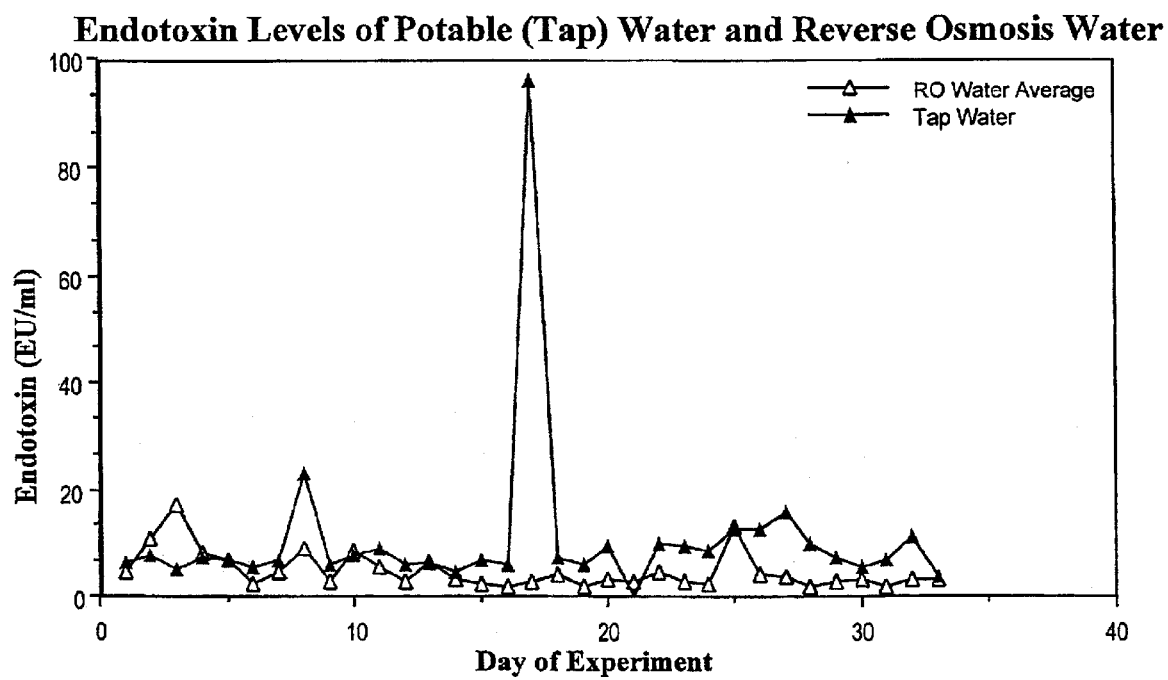
FIG. 1 is a diagram showing endotoxin levels in tap water and reverse osmosis (RO) water samples at the indicated days of operation as described in the preferred embodiments.

In a preferred embodiment, the source potable water is pre-purified by reverse osmosis which removes 95–98% of impurities including dissolved salts, colloids, microorganisms, endotoxin and other organic macromolecules. The endotoxin/pyrogen permeability of RO membranes varies and is also a function of the type of endotoxin present. There seems to be no correlation between the extent of endotoxin passage through the RO membrane and the endotoxin content of source potable water (FIG. 1). The RO unit may be protected by prefilters or adsorbents (charcoal and granular medium adsorbents) to remove some particulates and chlorine/chloramine from the source water. Besides RO membrane filtration, other membrane technologies, such as ultrafiltration or nanofiltration may also be used as an initial membrane filtration step.

A chemical sterilization is then performed using an immobilized iodine column. The column is made by adsorbing 0.1 N $KI_3$ to an agarose-based strong anion exchanger containing quaternary amine groups. A particularly preferred agarose-based strong anion exchanger is Q Ultraflow HX, manufactured by Sterogene Bioseparations, Inc. (Carlsbad, Calif.). The advantage of this sorbent is its extremely high affinity for iodine allowing the sterilization of about 10,000 bed volumes of water.

The iodine released by this column is subsequently reduced to iodide by another solid phase adsorbent that has thiol groups on an agarose-based adsorbent. A particularly preferred thiol-containing adsorbent for the reducing step is Thiol Ultraflow HX (Sterogene Bioseparations, Inc., Carlsbad, Calif.) made on the same highly crosslinked agarose support. The free iodine is instantaneously converted to iodide in a thiol-disulfide oxidation reaction.

Other solid phase reducing agents can potentially be utilized at this step such as immobilized phenols or conjugated alkenes. Other reducing agents that can be conjugated to a solid phase can alternatively be used; such reducing agents are described in M. B. Smith & J. March, "March's Advanced Organic Chemistry: Reactions, Mechanisms, and Structure" (5$^{th}$ ed., Wiley-Interscience, New York, 2001), pp. 1544–1568, incorporated herein by this reference.

Deionization is then performed to remove the iodide and residual dissolved salts and some of the endotoxin present. This process typically involves the use of ion exchange media that may take the form of particles, membranes or a combination of both. The ion exchange components require a pretreatment with 1 M HCl and 1 M NaOH, respectively to inactivate entrapped microorganisms and bacterial pyrogens. These solutions must be prepared in endotoxin-free, sterile water. The ion exchange components are subsequently rinsed free of acid and base with endotoxin-free, sterile water, mixed in the desired ratio and packed into a clean housing which may be a column or any other shaped container appropriate to carry out the deionization process. The deionization may also be performed in a system in which the deionizing components are continuously regenerated. This can be effected by electrolysis or any other suitable method.

In the next step, the purified water from deionization is perfused through an adsorbent which removes residual endotoxin or other pyrogens below the level of 0.25 EU/ml, specified in the US Pharmacopoeia for WFI, but preferably below 0.005 EU/ml, the sensitivity limit of the kinetic LAL assay. The adsorbent also adsorbs pyrogenic substances other than lipopolysaccharide (LPS) and may be prepared in the configuration of particles or membrane or a combination of both. The adsorbent is derivatized with a ligand having high affinity for endotoxin and binds pyrogens by a dual mechanism (hydrophobic interaction and ionic interactions). Preferably, the adsorbent that removes pyrogens is a polymeric support derivatized with a multiplicity of ligands that comprise a ($C_{10}$–$C_{24}$) alkylamino group and that specifically bind endotoxin. Preferably, the alkylamino group is a stearylamino group. Preferably, the polymeric support is agarose. At least a portion of the ligands can be crosslinked, such as by the use of 2,3-dibromopropanol. When the support is in the form of particles, the particles are preferably from about 20 to about 900 microns in diameter; more preferably, the particles are from about 60 to about 100 microns in diameter. Suitable adsorbents are disclosed in U.S. Pat. No. 6,106,723 to Grandics et al., which is incorporated herein in its entirety by this reference. A particularly preferred adsorbent is the adsorbent marketed as ClarEtox™, Clarigen, Inc., Carlsbad, Calif. An additional feature of this adsorbent is its cleanability with 1 M NaOH and that it is reusable at least 100 times after NaOH sanitization. This affords the required low cost, high throughput production of sterile, pyrogen-free water. In its most preferred embodiment, the ClarEtox particles are packed into a column and incubated overnight in 1 M NaOH followed by a wash with pyrogen-free, sterile water. The purified water from the deionization step is passed through the column and residual endotoxin is removed below the level specified by the Pharmacopoeia, practically below the limit of detection (Table 1).

Since non-LPS (LAL-negative) pyrogens also contribute to sample pyrogenicity, an assay other than the LAL test is necessary to evaluate pyrogens in the water samples. Such a test may be the USP rabbit pyrogen test. This, however, is rather tedious and impractical for this purpose. Moreover, the rabbit test does not provide information on sub-toxic, low level inflammatory reactions elicited by the sample. A more suitable test is based upon the peripheral blood mononuclear cell (PBMC) activation/cytokine assay that is equivalent to the rabbit test in assessing total pyrogenicity. PBMCs, when exposed to pyrogens, secrete inflammatory cytokines (IL-1, IL-6, IL-8, TNF-α, etc.) that can be detected at very low levels. This allows monitoring of the low level chronic inflammatory reactions that have eluded the rabbit test. The final purified water was also tested for TNF-α induction by the PBMC assay (FIG. 2).

Figure 2:
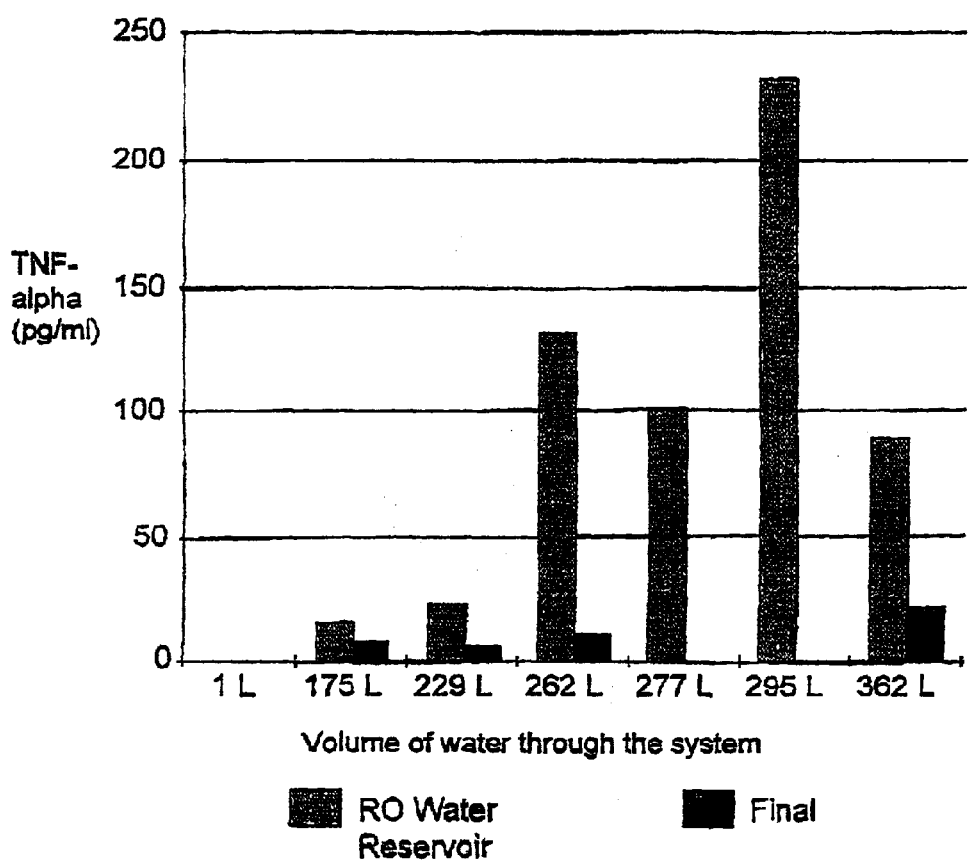
FIG. 2 shows the results of TNF-$\alpha$ assays in peripheral blood mononuclear cells induced by water as a measure of undesired pyrogenic contamination in the water. Peripheral blood mononuclear cells (PBMC) were prepared by Ficoll separation of peripheral blood, and non-adherent cells were removed during overnight culture in RPMI-1640 (containing 100 U/ml penicillin/streptomycin and 2 mM glutamine) supplemented with 20% fetal calf serum (FCS). The adherent cells were incubated in 6-well plates in 0.75 ml RPMI-1640 (2x) containing 6% FCS+0.75 ml tested sample from the RO water reservoir or the final water sample. Non-treated cells (0.75 ml Limulus amoebocyte lysate (LAL) water) were used as baseline TNF-$\alpha$ production (4.5 pg/ml) that was subtracted from each sample value. TNF-$\alpha$ was measured from the culture supernatant after 24-hr incubation, using an ELISA-kit according to manufacturer's instructions.

In a parallel experiment, the starting RO water was tested for endotoxin activity (LAL assay) (Table 1) and TNF-α induction in the PBMC assay (FIG. 2). In addition, the USP sterility test was performed at selected intervals to ensure sterility of the water product (Table 1). The endotoxin level was reduced below 0.005 EU/ml, a 4 logs reduction in LPS. The PBMC assay also showed greatly reduced TNF-α levels compared to the starting values. The sterility test results demonstrated the effectiveness of the sterilization procedure. Details of these experiments are disclosed in the Examples.

The conductivity of the water was also monitored at every stage of purification. The conductivity of tap (potable) water was around 1000 µS/cm. The RO step reduced it to 20–40 µS/cm that was reduced below 1–2µ S/cm by the deionization step. The endotoxin removing column did not affect water conductivity (Table 2).

TABLE 1

A. Endotoxin and Bacterial Culture Results

| Amount (L) | Endotoxin RO Reservoir (EU/mL) | Endotoxin Final (EU/mL) | Culture RO Reservoir (cfu/mL) | Culture Final (cfu/mL) |
|---|---|---|---|---|
| 1 | 0.006 | <0.005 | 0 | 0 |
| 11 | 0.007 | <0.005 | 0 | 0 |
| 62 | 0.007 | <0.005 | 0 | 0 |
| 83 | 0.016 | 0.006 | 1 | 0 |
| 134 | 0.009 | <0.005 | 1 | 0 |
| 155 | 0.021 | <0.005 | 1 | 0 |
| 175 | 0.015 | <0.005 | 0 | 0 |
| 229 | 0.023 | <0.005 | 0 | 0 |
| 247 | 0.025 | <0.005 | 0 | 0 |
| 262 | 0.028 | <0.005 | 0 | 0 |
| 277 | 0.332 | <0.005 | 0 | 0 |
| 295 | 0.362 | <0.005 | 32 | 0 |
| 310 | 0.440 | <0.005 | 60 | 0 |
| 325 | 0.549 | <0.005 | 260 | 0 |
| 335 | 0.229 | <0.005 | 338 | 0 |
| 347 | 0.370 | <0.005 | 22 | 0 |
| 362 | 0.387 | <0.005 | 105 | 0 |
| 377 | 0.511 | <0.005 | 36 | 0 |
| 392 | 0.807 | <0.005 | 0 | 0 |

TABLE 2

Conductivity Results

| Collection Amount (L) | Conductivity RO Reservoir (µS/cm) | Conductivity, Final (µS/cm) |
|---|---|---|
| 1 | 28.7 | 0.88 |
| 11 | 28.4 | 0.75 |
| 62 | 30.0 | 0.72 |
| 83 | 30.3 | 0.46 |
| 134 | 32.3 | 0.90 |
| 155 | 33.5 | 0.72 |
| 175 | 33.3 | 0.48 |
| 229 | 34.2 | 0.67 |
| 247 | 31.2 | 0.72 |
| 262 | 34.5 | 0.69 |
| 277 | 42.4 | 0.66 |
| 295 | 53.8 | 0.63 |
| 310 | 95.8 | 0.62 |
| 325 | 58.4 | 0.61 |
| 335 | 32.4 | 0.73 |
| 347 | 40.9 | 0.61 |
| 362 | 52.7 | 1.06 |

The purified sterile water can be used to make up dialysate, replacement fluid for CRRT or other sterile intravenous solutions, such as parenteral medicines. For example, the water produced meets the requirements for USP Purified Water, USP Sterile Purified Water, USP Water for Injection, USP Sterile Water for Injection, USP Sterile Water for Inhalation, USP Sterile Water for Irrigation, or USP Bacteriostatic Water for Injection.

A sterile ClarEtox column can also remove endotoxin from sterile solutions that are not free of endotoxin. An example to this is water for irrigation.

The following Examples illustrate the advantages of the subject invention. Accordingly, it is to be understood that the description in this disclosure is to facilitate comprehension of the invention and should not be construed to limit the scope thereof as persons skilled in the art can, in light of this disclosure, generate additional embodiments without exceeding the scope or departing from the spirit of the claimed invention.

EXAMPLE 1

Preparation of *Pseudomonas maltophilia* Supernatant:

*Pseudomonas maltophilia* was obtained from ATCC #17666 (Aug. 10, 1966), and the bacterial culture broth from Difco Laboratories (Detroit, Mich.). The culture was grown at 37° C. and LPS in the supernatant was monitored periodically by the LAL assay. The total culturing time was 48 h. Then the culture was refrigerated at 4° C. and centrifuged at 2,000× g. To the supernatant 20 µg/ml gentamycin (Sigma, St. Louis, Mo.) and 5 µg/ml ciprofloxacin (Bayer, West Haven, Conn.) were added. The supernatant was sterile filtered and aliquoted for freeze storage. The sterility of the filtrate was ascertained using agar-plate culture. No colony growth was observed. The LPS concentration was 24,000 EU/ml.

EXAMPLE 2

Preparation of Human Peripheral Blood Mononuclear Cells:

Approximately 25 ml blood was drawn from healthy volunteers. The mononuclear cells were isolated by Ficoll-Hypaque gradient centrifugation. After the separation step about $25 \times 10^6$ cells were obtained. The cells were resuspended in 10 ml PBS containing 1% BSA. The cells were adhered to a 6-well microtiter plate after resuspension in 20% fetal calf serum (FCS), RPMI-1640 at $2 \times 10^6$ cells/ml for 5 h at 37° C. in a 5% $CO_2$ atmosphere. After mild agitation the medium with non-adherent cells was removed, the cells counted and the number of adherent cells determined. Then 2 ml RPMI-1640 with 20% FCS supplement and 100 U/ml PenStrept solution were added followed by the necessary stimulant as endotoxin solution or the sterile filtrate, and ultrafiltered Pseudomonas supernatants as well as RO water samples. Each sample as well as the controls were incubated for 1.5–16 hr at 37° C. in a 5% $CO_2$ atmosphere. The supernatants were removed and tested for IL-8 induction.

EXAMPLE 3

Sandwich ELISA to Quantitate TNF-α Induction in Samples:

For the assays, the TNF-α ELISA-kit (Cell Sciences, Norwood, Mass.) was used. The readout is at 450 nm. The assay was performed following the manufacturer's directions.

EXAMPLE 4

Preparation of the Sterilizing Column:

The Q Ultraflow HX resin was packed into a 50 ml column and treated with 0.1 M NaOH overnight followed by a wash with sterile LAL water.

EXAMPLE 5

Preparation of the Reducing Column:

The Thiol Ultraflow HX resin was washed with 70% ethanol following its synthesis and then with sterile, LAL water and packed under a laminar flow hood into a 50-ml column

EXAMPLE 6

Preparation of Deionization Column:

Cation exchange resin was allowed to sit in 1 M NaOH overnight and anion exchange resin sit in 1 M HCl overnight. The resins were washed with sterile LAL water until neutrality and mixed together thoroughly. A 500 ml column was packed with the mixed resin. The column and all wetted parts were previously incubated in 1 M NaOH overnight and rinsed with sterile LAL water to neutrality.

EXAMPLE 7

Preparation of ClarEtox:

A column was packed with 50 ml of ClarEtox resin. At 3 ml/min 50 ml 1 M NaOH was pumped into the column and was allowed to sit in the column overnight. The column and the tubing were rinsed with sterile LAL water to neutrality.

EXAMPLE 8

The Water Purification System:

The RO water line was attached to the inlet port of the sterilizing column and water was passed through the column at 50 ml/min. This column was connected to the reducing column that converted iodine to iodide. The 500 ml bed volume deionizer column next in the line removed all iodide and other residual salts. The water was then flown onto a 50 ml ClarEtox column to strip all residual pyrogenic substances. Samples were taken throughout the run and sterility of the final water product was monitored using the USP sterility test. Besides, water conductivity, PBMC activation, and endotoxin were determined. It took 362 L of RO water before the sterilizing ability of the system was exhausted and bacterial breakthrough observed. This translates into about 8,000 ml of sterile water obtained on every ml of sterilizing resin. To ensure sterility of the final product water, an absolute bacterial filter is placed at the end of the system as a safeguard measure. The sterile, WFI grade water is subsequently used to prepare dialysate, replacement fluid for CRRT or other solutions for intravenous use.

ADVANTAGES OF THE INVENTION

The present invention provides a low-cost, efficient process for preparing water-for-injection grade sterile water that is free of pyrogens and organic contaminants. The water produced by the process of the present invention is particularly suitable for use in dialysis and other treatment methods in which large volumes of purified water are required.

Although the present invention has been described in considerable detail, with reference to certain preferred versions thereof, other versions and embodiments are possible. Therefore, the scope of the invention is determined by the following claims.

We claim:

1. A method for on-line, on-demand production of sterile, water-for-injection grade water comprising the steps of:
    (a) filtering the water by membrane filtration;
    (b) sterilizing the water by chemical sterilization using solid phase iodine;
    (c) reducing iodine released from the solid phase iodine to iodide;
    (d) deionizing the water to remove iodide, residual dissolved salts, and endotoxin and
    (e) removing pyrogens by perfusion through an adsorbent that removes pyrogens.

2. The method of claim 1 further comprising the step of filtering the water after removal of pyrogens in step (e) by a final filtration step.

3. The method of claim 1 wherein the membrane filtration of step (a) uses reverse osmosis.

4. The method of claim 1 wherein the membrane filtration of step (a) uses ultrafiltration or nanofiltration.

5. The method of claim 1 wherein the chemical sterilization using solid phase iodine is performed on an immobilized iodine column.

6. The method of claim 5 wherein the immobilized iodine column is prepared by adsorbing $KI_3$ to an agarose-based strong anion exchanger containing quaternary amine groups.

7. The method of claim 1 wherein the adsorbent that removes pyrogens is a polymeric support derivatized with a multiplicity of ligands that comprise a ($C_{10}$–$C_{24}$) alkylamino group and that specifically bind endotoxin.

8. The method of claim 7 wherein the alkylamino group is a stearylamino group.

9. The method of claim 7 wherein the polymeric support is agarose.

10. The method of claim 9 wherein the agarose is cross-linked.

11. The method of claim 7 wherein the support is in the form of particles.

12. The method of claim 11 wherein the particles are from about 20 to about 900 microns in diameter.

13. The method of claim 12 wherein the particles are from about 60 to about 100 microns in diameter.

14. The method of claim 7 wherein the adsorbent removes pyrogens below the level of 0.25 EU/ml.

15. The method of claim 14 wherein the adsorbent removes pyrogens below the level of 0.005 EU/ml.

16. A method for on-line, on-demand production of sterile, water-for-injection grade water comprising the steps of:
    (a) filtering the water by membrane filtration;
    (b) sterilizing the water by chemical sterilization using solid phase iodine on an immobilized iodine column prepared by adsorbing Kl3 to an agarose-based strong anion exchanger containing quaternary amine groups;
    (c) reducing iodine released from the solid phase iodine to iodide by using a solid phase adsorbent that has thiol groups on an agarose-based adsorbent;
    (d) deionizing the water to remove iodide, residual dissolved salts, and endotoxin;
    (e) removing pyrogens through an adsorbent that removes pyrogens and that is a polymeric cross-linked agarose support derivatized with a multiplicity of ligands that comprise a stearylamino group and that specifically bind endotoxin to remove pyrogens below the level of 0.005 EU/ml; and
    (f) filtering the water after the removal of pyrogens in step (e) with a final filtration step.

* * * * *